(12) United States Patent
Rinck et al.

(10) Patent No.: US 7,945,080 B2
(45) Date of Patent: May 17, 2011

(54) METHOD FOR VISUALIZING DAMAGE IN THE MYOCARDIUM

(75) Inventors: Daniel Rinck, Forchheim (DE); Michael Scheuering, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1485 days.

(21) Appl. No.: 11/335,617

(22) Filed: Jan. 20, 2006

(65) Prior Publication Data

US 2006/0241412 A1    Oct. 26, 2006

(30) Foreign Application Priority Data

Jan. 21, 2005 (DE) .......................... 10 2005 002 949

(51) Int. Cl.
*G06K 9/00* (2006.01)
*A61B 6/00* (2006.01)

(52) U.S. Cl. .......................................... 382/131; 378/8
(58) Field of Classification Search .......... 382/128–132; 378/4, 8, 15, 98.12, 901
See application file for complete search history.

(56) References Cited

U.S. PATENT DOCUMENTS

| | | | | |
|---|---|---|---|---|
| 5,050,227 A * | 9/1991 | Furusawa et al. | ............. | 382/269 |
| 6,171,246 B1 * | 1/2001 | Averkiou et al. | ............. | 600/458 |
| 6,373,920 B1 * | 4/2002 | Hsieh | ......................... | 378/98.11 |
| 6,461,303 B2 * | 10/2002 | Angelsen | ....................... | 600/458 |
| 6,496,560 B1 * | 12/2002 | Lin et al. | ............................ | 378/62 |
| 6,628,743 B1 * | 9/2003 | Drummond et al. | ............... | 378/8 |
| 7,260,252 B2 * | 8/2007 | Fujisawa | ....................... | 382/131 |
| 7,327,862 B2 * | 2/2008 | Murphy et al. | ................ | 382/128 |

FOREIGN PATENT DOCUMENTS

WO    WO 2004/003851 A2    1/2004

OTHER PUBLICATIONS

Lars Dornheim, Klaus D. Tönnies, Kat Dixon: Automatic Segmentation of the Left Ventricle in 3D SPECT Data by Registration with a Dynamic Anatomic Model. MICCAI 2005: 335-342.*
M.R. Kaus, J.V. Berg, J. Weese, W. Niessen and V. Pekar, "Automated segmentation of the left ventricle in cardiac MRI," Med. Image Anal., vol. 8(3), pp. 245-254, 2004.*

* cited by examiner

*Primary Examiner* — Vu Le
*Assistant Examiner* — Andrae S Allison
(74) *Attorney, Agent, or Firm* — Harness, Dickey & Pierce, P.L.C.

(57) ABSTRACT

A method is disclosed for visualizing damage in the myocardium. In such a method, CT image data of the heart are made available which were recorded with injection of contrast medium. The myocardium is isolated by segmentation from the CT image data. One or more views of the isolated myocardium are displayed on an image display device, density values being visualized with color coding in the display. At least one embodiment of the method permits visualization of damage of the myocardium based on CT image data, in which damaged areas of the myocardium can immediately be identified without time-consuming analysis.

7 Claims, 4 Drawing Sheets

METHOD FOR VISUALIZING DAMAGE IN THE MYOCARDIUM

The present application hereby claims priority under 35 U.S.C. §119 on German patent application number DE 10 2005 002 949.3 filed Jan. 21, 2005, the entire contents of which is hereby incorporated herein by reference.

FIELD

The present invention generally relates to a method for visualizing damage in the myocardium. With such a method it is possible, for example, to view infarct regions in the myocardium which are the result of cell areas with damaged cell membranes.

BACKGROUND

For displaying myocardial infarct regions, magnetic resonance tomography has hitherto mainly been used. So-called cardio MR is today still the established standard for visualization of heart wall diseases, since, in this technique, numerous methods such as MR perfusion or wall movement analyses are available which permit functional examination of the heart muscle (myocardium). In MR perfusion, MR images are recorded with injection of contrast medium. This permits the visualization of the contrast enhancement in the myocardium which occurs during the first rapid circulation of the injected contrast medium (so-called first-pass enhancement). This exploits the fact that the infarct region is due, pathophysiologically, to a cell area in which the cell membranes are completely or at least partially damaged by inadequate supply of oxygen, for example because of coronary stenosis. The contrast medium accumulates in these damaged areas, such that these areas are identifiable in the images.

The damaged infarct regions can in principle also be detected in the time interval of the first-pass enhancement by computed-tomography images, by visualizing the infiltration of the contrast medium into the heart muscle. The accumulation of the contrast medium in the damaged areas of the myocardium is reflected by narrow, irregularly described regions in the CT images which are generally visualized in MPR display (MPR: Multi-Planar Reformatting). However, these regions in the myocardium can be visually detected only with great difficulty, partly because of the proximity to the heart cavities filled with contrast medium, the so-called blood pool, because this blood pool in the same way delivers the high contrast generated by the contrast medium.

The only possible way of using cardio CT data of this kind for detecting infarct regions in the myocardium hitherto involved elaborate manual analysis of the regions of the heart muscle in the image data, and manual entry of regions of interest into a list. Manual construction of the standardized long and short axes of the heart was also necessary. This kind of evaluation, however, is too time-consuming for routine use.

U.S. Pat. No. 6,628,743 B1 discloses a method for acquiring and analyzing cardiac data, in which CT image data of the heart are made available which were recorded at different times after an injection of contrast medium. The method involves a segmentation of the myocardium based on common segmentation algorithms such as threshold methods, edge detection or region growing, in order to analyze the contrast medium enhancement at different times after the injection of contrast medium in the myocardium. This therefore involves comparison of CT images recorded at different times. Enhanced pixels can also be displayed in color.

WO 2004/003851 A2 is concerned with the display of parietal movements in a deformable 3D object, for example the heart, by way of a single image. In one example in the document, 3D ultrasound image data of the left ventricle of the heart are made available in order to display corresponding wall movements of the left ventricle. The wall of the left ventricle is here segmented from the image data by a segmentation technique in which a so-called "simplex mesh model" is adapted to the wall profile. This model involves a surface which is represented in the form of a mesh and which is adapted to the profile of the left ventricle in the ultrasound image data. For this purpose, however, the wall profile must already be to some extent apparent in the image data.

SUMMARY

An object of at least one embodiment of the present invention is to provide a method for visualizing damage in the myocardium on the basis of CT image data, with which method the damage can be identified without time-consuming manual analysis of the image data.

An object may be achieved by a method. Advantageous refinements of the method can be gathered from the following detailed description and from the illustrative embodiments.

In the method of at least one embodiment, CT image data of the heart are made available which were recorded with injection of contrast medium. For the image recording, a time is chosen at which contrast enhancement occurs in the myocardium as a result of the first rapid circulation of the injected contrast medium (first-pass enhancement). The myocardium is then isolated by segmentation in the CT image data, a 3D image data record.

The segmentation is first performed by adaptation of a suitable model of the heart muscle. After the isolation of the myocardium in the CT image data, it is displayed on an image display device, isolated into one or more predefined views. The display is in color, with different color coding of voxels and pixels which are attributable to CT density values in different density ranges. In an example, in addition to these color-coded views, the corresponding gray-scale views of the isolated myocardium are also shown.

Preferably, when using the model-based segmentation technique, the standardized short and long axes of the heart are also determined and assigned to the isolated image data of the myocardium. This permits a standardized display of the myocardium in sectional planes perpendicular to the long axis and perpendicular to the short axis of the heart. The display itself can, for example, be as a slice image or in MPR.

By use of the isolated display of the myocardium in conjunction with the color coding, damaged areas enhanced with contrast medium, in particular areas of damage to the cell membrane resulting from an infarct, can immediately be clearly identified. The masking-out of the adjacent areas, in particular of the blood pool lying close by and likewise filled with contrast medium, avoids complicated analysis of the image data.

By color coding, it is possible to display a greater value range than is possible in a gray-scale display. In this way, the sometimes narrow and irregular areas enhanced with contrast medium can be highlighted very clearly, for example in red, in the individual views. The method thus permits a routine identification of contrast enhancement in the myocardium from CT image data in a manner that is not time-consuming.

The segmentation of the CT image data is performed on the basis of a heart model. Modern image processing provides various methods permitting modeling of anatomical structures. For example, so-called "Active Shape Models" (ASM)

and "Point Distribution Models" (PDM) are known from T. F. Cootes et al., "Statistical Models of Appearance for Computer Vision", University of Manchester, Dec. 5, 2000, the entire contents of which are hereby incorporated herein by reference. These methods make it possible to generate a standard description of the structure, for example of the heart muscle, from a set of training data and, building on this standard description, to generate corresponding deviations of the model or individual adjustments to predeterminable data.

In addition, these models can also be worked intuitively using simple tools of interaction, for example using 3D point shift tools, in order to refine the adaptation. If such a model is used in the method of at least one embodiment, it is possible to model the interface between the myocardium and the blood volume of the left ventricle enhanced with contrast medium. Since the model has learnt the information on the shape of the structure in question on the basis of the training data, it is able to set the boundary between two structures which have similar HU values, as is the case here in the separation between the enhanced myocardium and the left ventricle filled with contrast medium.

BRIEF DESCRIPTION OF THE DRAWINGS

Embodiments of the present method are explained in more detail again below on the basis of an illustrative embodiment in conjunction with the drawings and without limiting the scope of protection prescribed by the patent claims. In the drawings:

DETAILED DESCRIPTION OF THE EXAMPLE EMBODIMENTS

Figure 1:
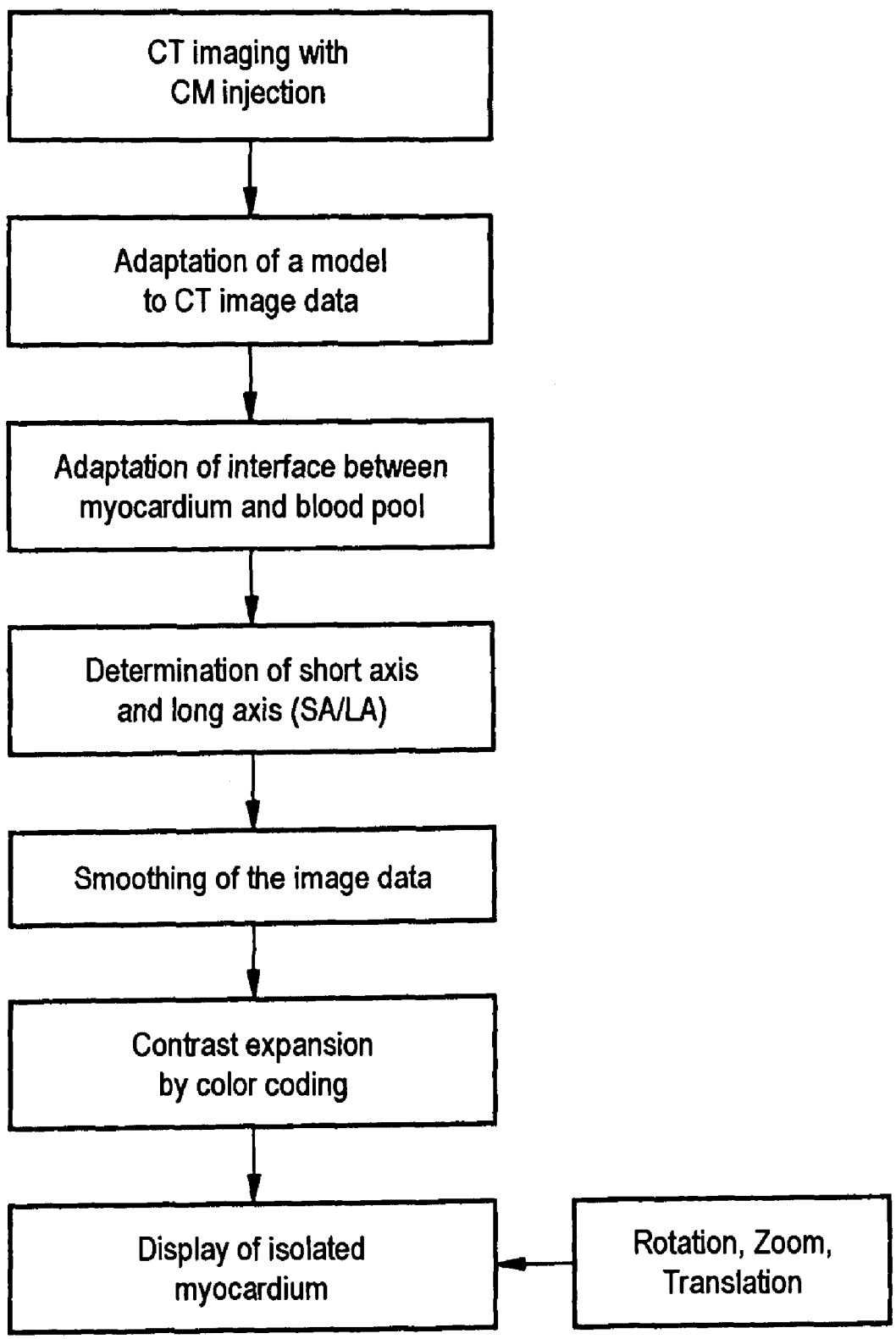
FIG. 1 shows an example of the sequence of method steps in an embodiment of the method.

An example of the sequence of method steps in at least one embodiment of the present method is shown in FIG. 1 and is also explained in detail below in conjunction with the other figures. First, CT image data of the heart are made available by way of CT imaging with injection of contrast medium, these showing the first-pass enhancement in the myocardium. These CT image data are then subjected to segmentation in order to isolate the myocardium, and the CT image data assigned to the myocardium, from the data record.

An ASM surface model is used, as is known, for example, from the aforementioned publication by T. F. Cootes et al. Since the model describes only the surfaces, i.e. the epicardium and endocardium, all voxel values that lie between these surfaces have to be isolated in a first stage. All other voxels of the image data record are masked and no longer displayed.

Since the model takes shape criteria into account, it is unable to describe the edge between the left ventricle and the myocardium as clearly as does an isolated region-based or edge-based segmentation technique. For this reason, in the present illustrative embodiment, the margin of the myocardium toward the blood volume is in addition adaptively isolated.

To do this, a morphological dilation is implemented in which the mask of the blood volume is widened in steps, in each case by one voxel layer. For each new voxel layer to be applied, a check is made as to whether the newly arrived area still belongs to the blood volume. This check can be made on the basis of a gray-scale value criterion or texture measures. The check is carried out voxel by voxel. The algorithm stops when more than 50% of the voxels in the environment of the respective voxel are attributed to the myocardium. In this way, the interface between the myocardium and the blood-filled left ventricle can be modeled and refined still mere accurately in relation to the profile of this interface obtained by the model.

In the previous analysis of the image data in accordance with the prior art, the radiologist himself had to set the desired direction of viewing (along the long heart axis and short heart axis) using the MPRs. In the present example, the information items required for this are already inherently present in the model of the left ventricle, with the result that the long heart axis and the short heart axis can be automatically determined and assigned to the image data. For this reformatting of the image data, the short heart axis is oriented perpendicularly with respect to the long main axis of the model. The horizontal long axis is perpendicular with respect to the short heart axis. Both axes may then have to be turned slightly on the basis of the spatial information items from the DICOM coordinates system in order to provide the image impression to which the radiologist is accustomed.

Since the image data are generally very noisy, especially in the case of overweight patients, they should be smoothed before displaying the image. In the present example, a tangential smoothing of the image data is performed. For this purpose, the shape of the myocardium in sections perpendicular to the short heart axis is assumed as a circle shape and broken into rings of different radii. The smoothing is then performed always only along the rings or along the tangent to the respective ring. This prevents the smoothing acting from one ring to the other. Transmural infarct regions can thus be reliably smoothed. This tangential smoothing avoids incorrect diagnosis in cases where the infarct region extends across the entire width of the myocardium. Smoothing in the radial direction would in this case cause too much blurring of the edge areas of the infarct.

The reformatted and smoothed image data are then subjected to a contrast expansion. In this step, small HU ranges of the CT density values on which the image data are based are projected onto a color scale and the image data are presented in the desired view with suitable color coding. This permits the visualization even of very small changes in the HU value range.

Figure 2:
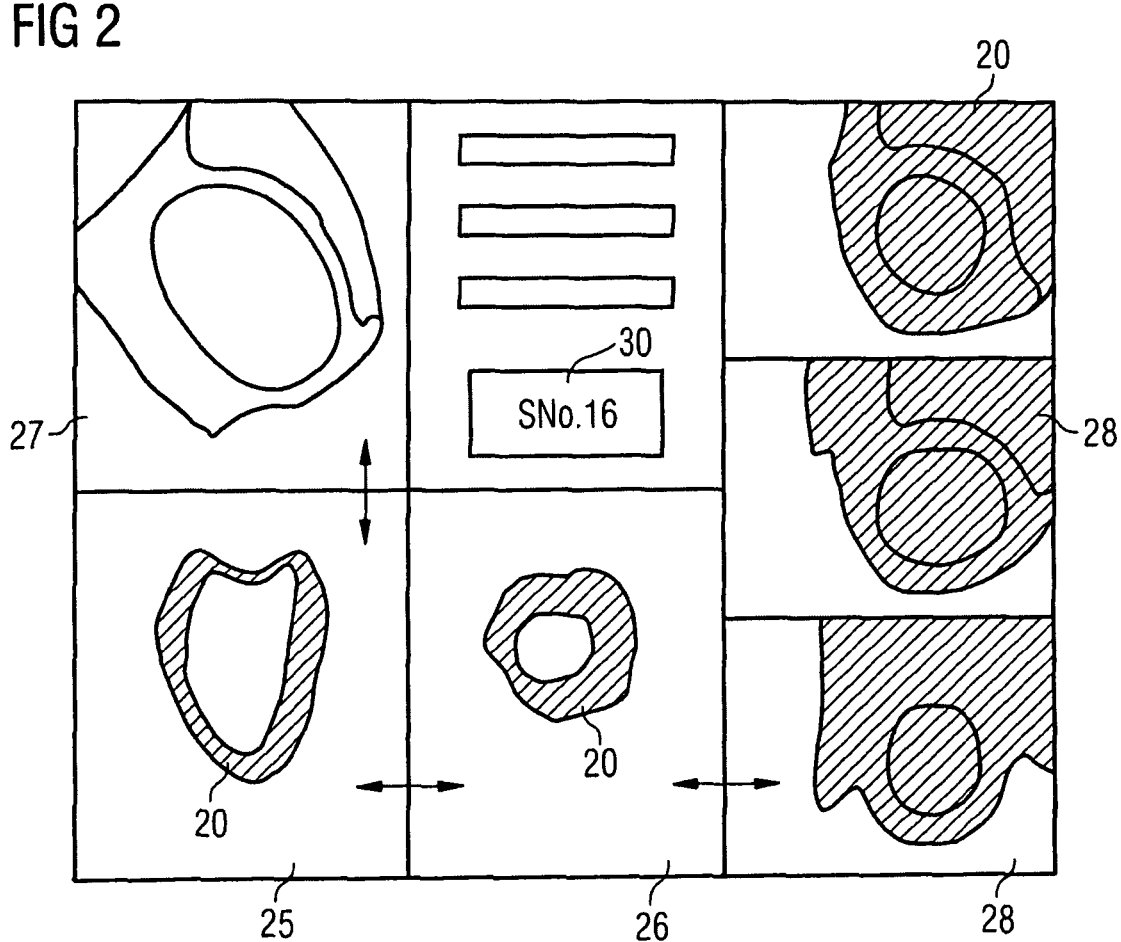
FIG. 2 shows an example of the display of the isolated myocardium in accordance with an embodiment of the method.

FIG. 2 shows an example of a display of the color-coded images in different views on a screen. Here, an MPR display of the isolated myocardium 20 is visualized in a section on the long axis (image 25) and in a section on the short axis (image 26), next to one another. The non-color-coded MPRs 28 are also displayed in the short heart axis and the long heart axis. The user can now rotate, zoom into and move the views in any desired manner. As is indicated by the double arrows in FIG. 2, all the displays are always altered in synchronization. The instantaneous position can be monitored in a 3D display 27 of the heart model and of the active plane.

Figure 4:
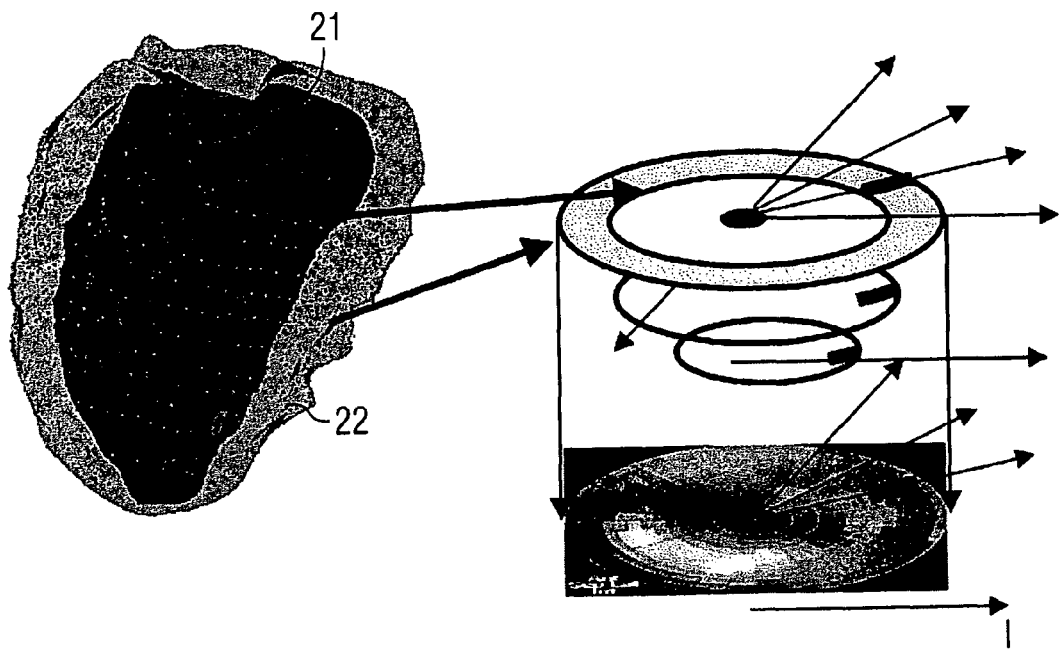
FIG. 4 shows an example of a polar map display of the left ventricle with the heart muscle.

It is also possible to show the contrast enhancement of the heart muscle in a "bull's eye plot" view (polar map) customary for functional diagnosis. Here, the individual rings or shells of the myocardium from apex to base are projected into a plane and in this way permit display of the whole heart muscle in a 2D image. The method of contrast expansion can be used in the same way in this display. FIG. 4 shows, on the left-hand side, a view of the adapted model of the myocardium, which comprises only the epicardium 21 and the endocardium 22. The polar map display is indicated on the right-hand side of the figure, which illustrates the projection of the individual shells or rings of the myocardium in one plane.

Figure 3:
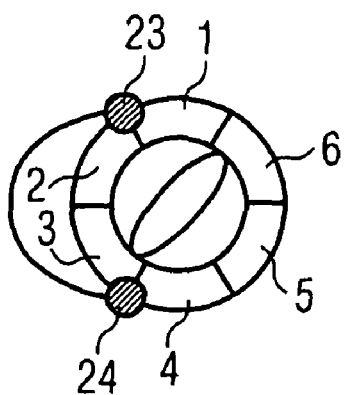
FIG. 3 shows an example of the interactive marking of the anterior septum and posterior septum in accordance with an embodiment of the method.
Figure 3:
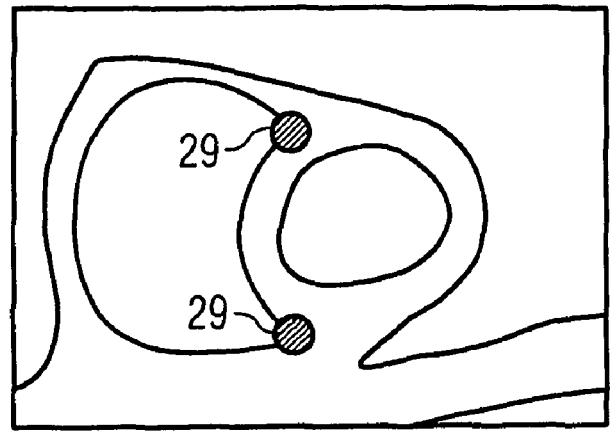
Figure 3:
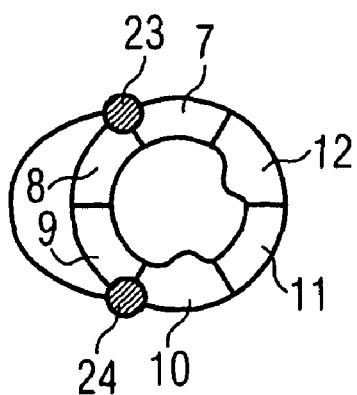
Figure 3:
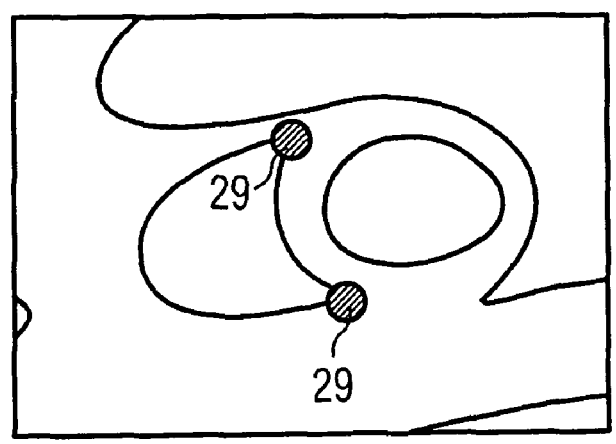
Figure 3:
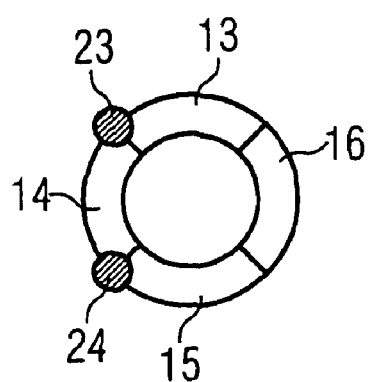
Figure 3:
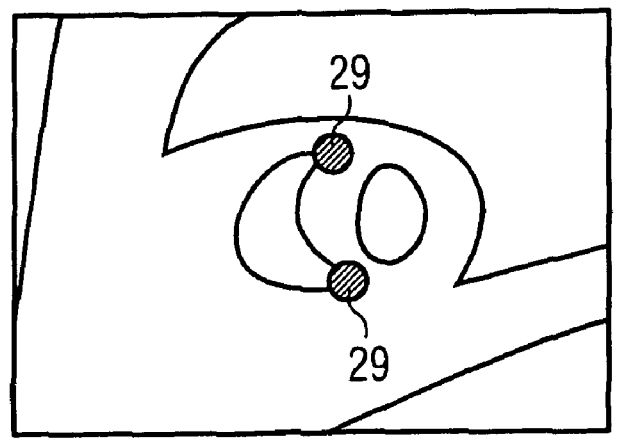

In a further embodiment of the present method, the user is requested to mark the anterior septum 23 and the posterior septum 24 in apical, in mid-ventricular and in basal short-axis orientation in the images. This is indicated in FIG. 3, which shows the corresponding marking points 29 in the MPR images of said sectional planes.

Figure 5:
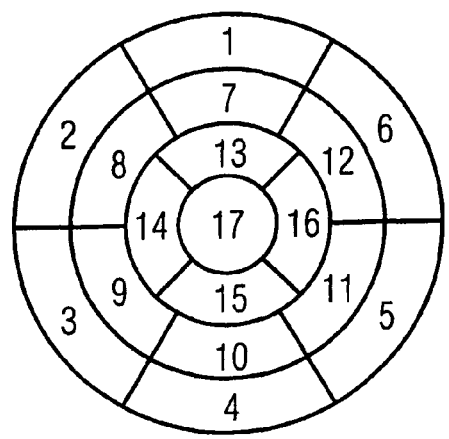
FIG. 5 shows the 17-segment model of the AHA.

Based on this interactive marking, the isolated myocardium can be divided into the segments of the so-called 17-segment model (AHA after the American Heart Association), which is shown in FIG. 5. Following this automatic division, the viewer is now able to use a graphic input device, for example a mouse, to click on any desired area of suspicion in the displayed images and to mark any desired areas. For each click, the corresponding position in the AHA segment model is indicated in a window 30. The user can additionally enter observations or comments which are stored, in conjunction with the marked position, as a report. The corresponding colored or non-colored image can also be stored in the same way.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing damage in the myocardium, comprising:
    making available CT image data of a heart, previously recorded after injection of contrast medium at a time when contrast enhancement occurs in the myocardium as a result of the first rapid circulation of the injected contrast medium;
    segmenting the CT image data to isolate the myocardium;
    tangentially smoothing the image data, the tangential smoothing of the image data being performed on sectional images of the isolated myocardium, oriented perpendicular to a short axis of the heart; and
    displaying at least one view of the isolated myocardium on an image display device, with CT density values being color-coded such that damaged areas enhanced with contrast medium are easily identifiable, the segmenting being done by adaptation of a model of the heart muscle, and an interface, obtained from the adaptation of the model, between the myocardium and adjacent areas being adapted with greater accuracy via a segmentation technique based on examination of individual voxels.

2. The method as claimed in claim 1, wherein a standardized long axis and the short axis of the heart are calculated automatically from the model and are set in relation to the image data.

3. The method as claimed in claim 1, wherein a segment model of the heart is assigned to the image data after an interactive marking of boundary points of the septum, and, when an image area of one of the displayed views is marked, the associated segment is automatically labeled on the image display device.

4. The method as claimed in claim 2, wherein a segment model of the heart is assigned to the image data after an interactive marking of boundary points of the septum, and, when an image area of one of the displayed views is marked, the associated segment is automatically labeled on the image display device.

5. A method for visualizing damage in the myocardium based upon CT image data of the heart, previously recorded after injection of contrast medium, the method comprising:
    isolating the myocardium in the CT image data;
    tangentially smoothing the image data, the tangential smoothing of the image data being performed on sectional images of the isolated myocardium, oriented perpendicular to a short axis of the heart; and
    displaying at least one view of the isolated myocardium, with CT density values being color-coded such that damaged areas enhanced with contrast medium are easily identifiable, the isolating being done by adaptation of a model of the heart muscle, and an interface, obtained from the adaptation of the model, between the myocardium and adjacent areas being adapted with greater accuracy via a segmentation technique based on examination of individual voxels.

6. The method as claimed in claim 5, wherein a standardized long axis and the short axis of the heart are calculated automatically from the model and are set in relation to the image data.

7. The method as claimed in claim 5, wherein a segment model of the heart is assigned to the image data after an interactive marking of boundary points of the septum, and, when an image area of one of the displayed views is marked, the associated segment is automatically labeled on the image display device.

* * * * *